US012560559B2

(12) United States Patent
Edwards et al.

(10) Patent No.: US 12,560,559 B2
(45) Date of Patent: Feb. 24, 2026

(54) STORED GRAIN INVENTORY MANAGEMENT NEURAL NETWORK

(71) Applicant: University of Manitoba, Winnipeg (CA)

(72) Inventors: Keeley Akiko Edwards, Winnipeg (CA); Ian Jeffrey, Winnipeg (CA); Colin Gerald Gilmore, Winnipeg (CA); Joe LoVetri, Winnipeg (CA); Mohammad Asefi, Winnipeg (CA); Nicholas Geddert, Winnipeg (CA); Kennedy Krakalovich, Winnipeg (CA); Ryan Kruk, Winnipeg (CA)

(73) Assignee: University of Manitoba, Winnipeg (CA)

( * ) Notice: Subject to any disclaimer, the term of this patent is extended or adjusted under 35 U.S.C. 154(b) by 287 days.

(21) Appl. No.: 18/042,593

(22) PCT Filed: Jul. 27, 2021

(86) PCT No.: PCT/IB2021/056810
§ 371 (c)(1),
(2) Date: Feb. 22, 2023

(87) PCT Pub. No.: WO2022/038437
PCT Pub. Date: Feb. 24, 2022

(65) Prior Publication Data
US 2023/0280286 A1 Sep. 7, 2023

Related U.S. Application Data

(60) Provisional application No. 63/071,495, filed on Aug. 28, 2020.

(51) Int. Cl.
| | | |
|---|---|---|
| *G01N 22/04* | (2006.01) | |
| *G01N 33/02* | (2006.01) | |
| *G06N 3/08* | (2023.01) | |

(52) U.S. Cl.
CPC ............. *G01N 22/04* (2013.01); *G01N 33/02* (2013.01); *G06N 3/08* (2013.01)

(58) Field of Classification Search
None
See application file for complete search history.

(56) References Cited

U.S. PATENT DOCUMENTS 9,772,294 B2    9/2017  Holden et al.
10,175,109 B2 *  1/2019  Perkins ................. G01N 21/31
(Continued)

OTHER PUBLICATIONS

Gilmore Colin et al: "Phaseless Parametric Inversion for System Calibration and Obtaining Prior Information", IEEE Access, vol. 7, Sep. 5, 201 pp. 128735-128745, XP011746478, DOI: 10.1109/ACCESS.2019.2939725.
(Continued)

*Primary Examiner* — Mark A Shabman
(74) *Attorney, Agent, or Firm* — Kyle Satterthwaite; Ryan Dupuis; Ade & Company Inc.

(57) ABSTRACT

In one embodiment, a system, comprising: one or more processors; and a memory comprising instructions, wherein the one or more processors are configured by the instructions to: receive first electromagnetic data at a plurality of frequencies; process the first electromagnetic data; and generate prediction parameters by passing the processed first electromagnetic data through a neural network trained on data corresponding to a synthetic training set, the prediction parameters corresponding to a container and contents located within the container.

18 Claims, 9 Drawing Sheets

(56)         References Cited

U.S. PATENT DOCUMENTS

| | | | | |
|---|---|---|---|---|
| 2004/0031335 A1* | 2/2004 | Fromme | ................. | G01F 22/00 |
| | | | | 73/865 |
| 2012/0019406 A1* | 1/2012 | Sarkis | ..................... | G01S 13/89 |
| | | | | 342/22 |
| 2017/0184508 A1* | 6/2017 | Holden | .................. | G01N 21/94 |
| 2017/0184509 A1* | 6/2017 | Holden | ............... | G01N 33/383 |
| 2024/0183799 A1* | 6/2024 | Asefi | ...................... | G01N 22/04 |
| 2025/0314608 A1* | 10/2025 | Anderson | .............. | G01N 27/24 |

OTHER PUBLICATIONS

Chen Xudong et al: "A Review of Deep Learning Approaches for Inverse Scattering Problems (Invited Review)", Electromagnetic waves (Cambridge, Mass.), Jan. 1, 2020 (Jan. 1, 2020), pp. 67-81, XP055853514, DOI: 10.2528/PIER20030705 Retrieved from the Internet: URL:https://www.jpier.org/PIER/ pier167/07.20030705. pdf.

Asefi Mohammad et al: "Grain bin monitoring via electromagnetic imaging", Computers and Electronics in Agriculture, Elsevier, Amsterdam, NL, vol. 119, Nov. 5, 2015 (Nov. 5, 2015), pp. 133-141, XP029320918, ISSN: 0168-1699, DOI: 10.1016/J.COMPAG.2015. 10.016.

Sandhu A I et al: "A Neural Network Assisted Greedy Algorithm For Sparse Electromagnetic Imaging", arxiv.org, Cornell University Library, 201 Olin Library Cornell University Ithaca, NY 14853, Nov. 15, 2019 (Nov. 15, 2019), XP081533075.

UK Intellectual Property Office, Search report for related UK Application No. GB2014465.5, dated Feb. 22, 2021, 3 pages.

European Patent Office, International Search Report related to International Patent Application No. PCT/IB2021/056810, mail date Nov. 2, 2021, 13 pages.

* cited by examiner

100

$h$ = height of grain at bin wall $\Phi$ = angle of grain repose $\epsilon$ = average complex permittivity of the grain $$\epsilon = \epsilon_0(\epsilon_r + j\epsilon_i)$$

104

106
RECEIVE FIRST ELECTROMAGNETIC DATA AT A PLURALITY OF FREQUENCIES

108
PROCESS THE FIRST ELECTROMAGNETIC DATA

110
GENERATE PREDICTION PARAMETERS BY PASSING THE PROCESSED FIRST ELECTROMAGNETIC DATA THROUGH A NEURAL NETWORK TRAINED ON DATA CORRESPONDING TO A SYNTHETIC TRAINING SET

STORED GRAIN INVENTORY MANAGEMENT NEURAL NETWORK

CROSS REFERENCE TO RELATED APPLICATIONS

This application claims the benefit of U.S. Provisional Application No. 63/071,495, filed Aug. 28, 2020, which is hereby incorporated by reference in its entirety.

TECHNICAL FIELD

The present disclosure is generally related to electromagnetic imaging of containers.

BACKGROUND

Imaging contents within a container is a powerful tool, especially when the interior of the container is difficult to access. In the case of grain bin monitoring, knowledge of the grain/air surface, once obtained, provides the volume of grain in the bin, which is of significant economic importance to anyone storing grain in bins. Once grain volume is known, existing methods may be used to calculate the weight of the contents of the bin. Grain is bought and sold by weight. One type of grain bin monitoring technology, referred to as electromagnetic inversion or imaging, uses radio-frequency signals, a series of antennas placed inside of a grain bin, and an inversion (or imaging) algorithm to create an image of the electrical permittivity of the contents of the bin. The electrical permittivity may be used to determine the moisture contents of the grain stored in a bin. The imaging/inversion algorithm requires that a computer model of the bin and antennas be constructed, though this model has inevitable errors. These errors (called modelling errors) require the raw radio-frequency data to be calibrated before the data can be used to generate an image.

Accordingly, electromagnetic inversion systems require that experimental data be calibrated to the computational inversion model being used, and that accurate prior information be provided to the inversion algorithm to enable higher-quality images. However, for some applications of inversion, known calibration targets cannot be easily introduced into the imaging region. Also, the ability to determine prior information may be limited.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DESCRIPTION OF EXAMPLE EMBODIMENTS

Overview

Figure 1:
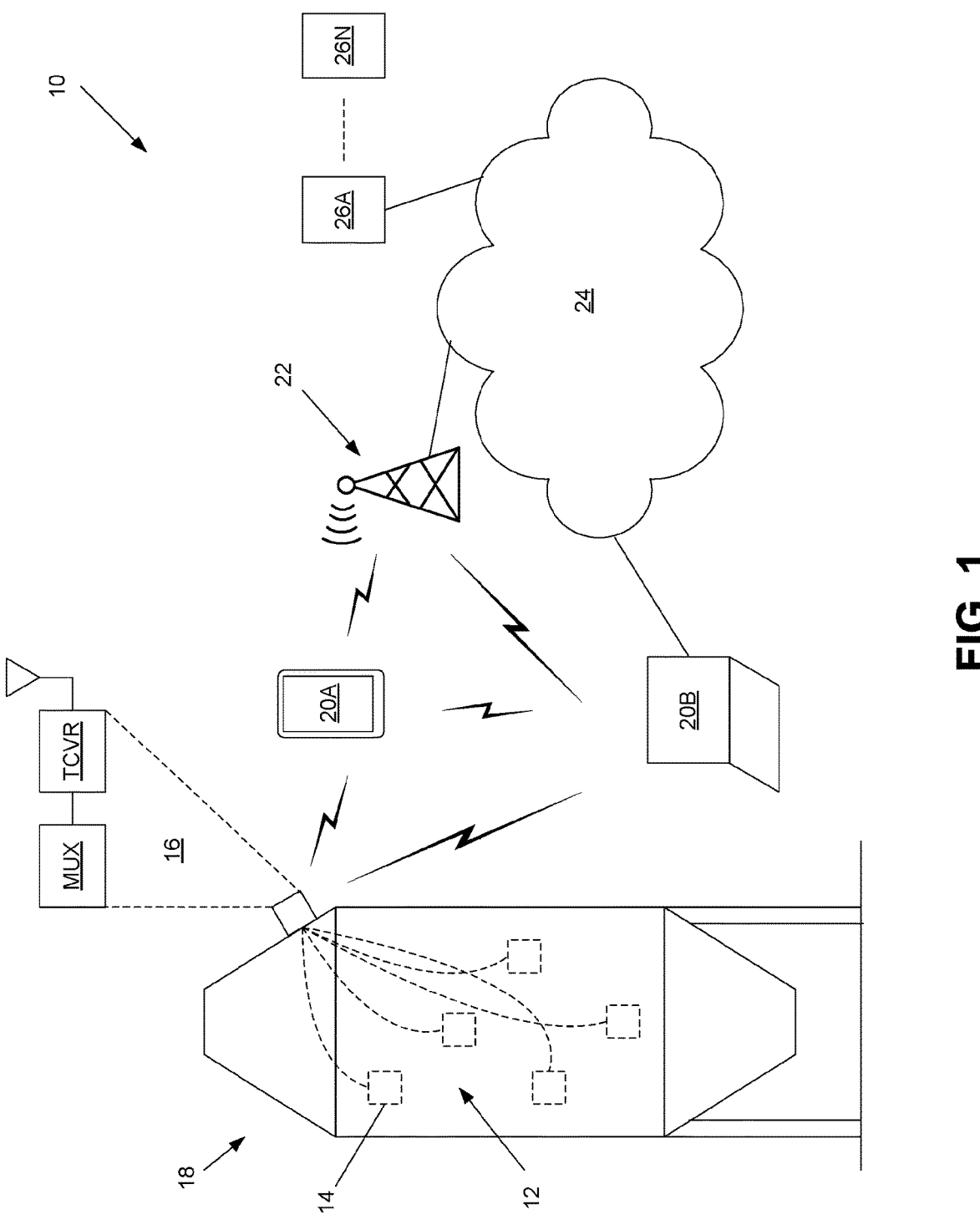
FIG. 1 is a schematic diagram that illustrates an example environment in which an embodiment of a neural network-based parametric inversion system may be implemented.

In one embodiment, a system, comprising: one or more processors; and a memory comprising instructions, wherein the one or more processors are configured by the instructions to: receive first electromagnetic data at a plurality of frequencies; process the first electromagnetic data; and generate prediction parameters by passing the processed first electromagnetic data through a neural network trained on data corresponding to a synthetic training set, the prediction parameters corresponding to a container and contents located within the container.

Detailed Description

Certain embodiments of a neural network-based parametric inversion system and method that use uncalibrated data to estimate the contents within a container and derive values for the formulation of a pixel-based inversion are disclosed. For instance, the neural network-based parametric inversion system may be used to derive information about grain in a grain storage bin. In one embodiment, the neural network-based parametric inversion system rapidly determines the height and volume of grain in the bin to characterize the grain/air interface, and provides bulk permittivity estimates (e.g., parameters) of the bin contents that may be used to provide an estimate of moisture content of the grain. This information may also be used to calibrate the system and provide an initial guess, enabling full inversion. In one embodiment, a neural network is trained solely on synthetic data, and can determine the parameters from uncalibrated experimental (measurement) data. In some embodiments, a neural network may be trained on a mix of synthetic data and experimental data, or assuming a sufficient amount of experimental data, the training may be based on experimental data in some embodiments.

Digressing briefly, some electromagnetic inversion-based grain bin monitoring techniques require that experimental data be calibrated (e.g., via physical access to the container) to the computational inversion model being used, and that accurate prior information be provided to the inversion algorithm to enable higher-quality images. Such techniques are burdensome for applications where access to the container is challenging and prior information is not sufficient or available. In a related, commonly-owned utility application entitled, "Electromagnetic Imaging and Inversion of Simple Parameters in Storage Bins", based on U.S. Provisional applications 62/870,254 (filed Jul. 3, 2019) and 62/892,130 (filed Aug. 27, 2019), and incorporated herein by reference, a similar problem is solved yet in a different way, using simple parameter inversion that takes the data (prior to full reconstruction), and characterizes the grain/air interface and average permittivity of the grain in the bin as a simple parameter set through hundreds of forward solver calls for each data set. More specifically, the method described in the commonly-owned applications extract bulk parameters via a phaseless parametric inversion of the electromagnetic data using a gradient-free optimization method that repeatedly calls the forward model. Though that method demonstrates that an appropriately selected, phaseless objective function can compensate for the inability to calibrate the system, it is computationally expensive, requiring several hours of multi-core servers to generate bulk parameter estimates. Further, since computational time scales directly with the number of frequencies used to determine the bulk parameters, parametric inversion is typically run at a single frequency to minimize computational time, though additional frequencies can add important information that leads to robustness and raw-data noise reduction. Once the bulk parameters are estimated, a full inversion technique requires additional time (e.g., using Contrast Source Inversion). In contrast, certain embodiments of a neural network-based parametric inversion system provides an advantage in that it allows for the determination of parameters from an experimental measurement in a matter of seconds, providing a long-term cost benefit over existing parameter inversion methods. That is, the neural network method may require a high computational cost up front, requiring many forward solver calls to generate the training set, however, once the network is trained, there is very little computational cost or time required to process a measurement. In other words, certain embodiments of a neural network-based parametric inversion system may process a measurement hundreds of times faster than existing technology. In exchange for this marked increase in speed, there is a high upfront computational cost associated with creating the training set and training the network, yet the upfront cost to performance boost ratio decreases each time a measurement is processed.

Further, similar to the phase-less parametric inversion method described above, the neural network-based parametric inversion system does not need to introduce a target or calibration object into the imaging region. The use of magnitude data enables comparisons of measurements and simulations without traditional calibration. The magnitude data enables estimates of permittivity information (real and imaginary values) of the grain and other geometrical information pertaining to the grain volume within the container that simulates calibration data and prior information, which when further processed using a calibration equation, can be used to implement a pixel-based inversion.

Having summarized certain features of a neural network-based parametric inversion system of the present disclosure, reference will now be made in detail to the description of a neural network-based parametric inversion system as illustrated in the drawings. While a neural network-based parametric inversion system will be described in connection with these drawings, there is no intent to limit it to the embodiment or embodiments disclosed herein. For instance, in the description that follows, one focus is on grain bin monitoring. However, certain embodiments of a neural network-based parametric inversion system may be used to determine other contents of a container, including one or any combination of other materials or solids, fluids, or gases, as long as such contents reflect electromagnetic waves. Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents included within the spirit and scope of the disclosure as defined by the appended claims. Further, it should be appreciated in the context of the present disclosure that the claims are not necessarily limited to the particular embodiments set out in the description.

FIG. 1 is a schematic diagram that illustrates an example environment 10 in which an embodiment of a neural network-based parametric inversion system may be implemented. It should be appreciated by one having ordinary skill in the art in the context of the present disclosure that the environment 10 is one example among many, and that some embodiments of a neural network-based parametric inversion system may be used in environments with fewer, greater, and/or different components than those depicted in FIG. 1. The environment 10 comprises a plurality of devices that enable communication of information throughout one or more networks. The depicted environment 10 comprises an antenna array 12 comprising a plurality of antenna probes 14 and an antenna acquisition system 16 that is used to monitor contents within a container 18 and uplink with other devices to communicate and/or receive information. The container 18 is depicted as one type of grain storage bin (or simply, grain bin), though it should be appreciated that containers of other geometries, for the same (e.g., grain) or other contents, with a different arrangement (side ports, etc.) and/or quantity of inlet and outlet ports, may be used in some embodiments. As is known, electromagnetic imaging uses active transmitters and receivers of electromagnetic radiation to obtain quantitative and qualitative images of the complex dielectric profile of an object of interest (e.g., here, the contents or grain).

As shown in FIG. 1, multiple antenna probes 14 of the antenna array 12 are mounted along the interior of the container 18 in a manner that surrounds the contents to effectively collect the scattered signal. For instance, each transmitting antenna probe is polarized to excite/collect the signals scattered by the contents. That is, each antenna probe 14 illuminates the contents while the receiving antennas probes collect the signals scattered by the contents. The antenna probes 14 are connected (via cabling, such as coaxial cabling) to a radio frequency (RF) switch matrix or RF multiplexor (MUX) of the antenna acquisition system 16, the switch/mux switching between the transmitter/receiver pairs. That is, the RF switch/mux enables each antenna probe 14 to either deliver RF energy to the container 18 or collect the RF energy from the other antenna probes 14. The switch/mux is followed by an electromagnetic transceiver (TCVR) system of the antenna acquisition system 16 (e.g., a vector network analyzer or VNA). The electromagnetic transceiver system generates the RF wave for illumination of the contents of the container 18 as well as receiving the measured fields by the antenna probes 14 of the antenna array 12. As the arrangement and operations of the antenna array 12 and antenna acquisition system 16 are known, further description is omitted here for brevity. Additional information may be found in the publications "Industrial scale electromagnetic grain bin monitoring", *Computers and Electronics in Agriculture*, 136, 210-220, Gilmore, C., Asefi, M., Paliwal, J., & LoVetri, J., (2017), "Surface-current measurements as data for electromagnetic imaging within metallic enclosures", *IEEE Transactions on Microwave Theory and Techniques*, 64, 4039, Asefi, M., Faucher, G., & LoVetri, J. (2016), and "A 3-d dual-polarized near-field microwave imaging system", *IEEE Trans. Microw. Theory Tech.*, Asefi, M., OstadRahimi, M., Zakaria, A., LoVetri, J. (2014).

Note that in some embodiments, the antenna acquisition system 16 may include additional circuitry, including a global navigation satellite systems (GNSS) device or triangulation-based devices, which may be used to provide location information to another device or devices within the environment 10 that remotely monitors the container 18 and associated data. The antenna acquisition system 16 may include suitable communication functionality to communicate with other devices of the environment.

The uncalibrated, raw data collected from the antenna acquisition system 16 is communicated (e.g., via uplink functionality of the antenna acquisition system 16) to one or more devices of the environment 10, including devices 20A and/or 20B. Communication by the antenna acquisition system 16 may be achieved using near field communications (NFC) functionality, Blue-tooth functionality, 802.11-based technology, satellite technology, streaming technology, including LoRa, and/or broadband technology including 3G, 4G, 5G, etc., and/or via wired communications (e.g., hybrid-fiber coaxial, optical fiber, copper, Ethernet, etc.) using TCP/IP, UDP, HTTP, DSL, among others. The devices 20A and 20B communicate with each other and/or with other devices of the environment 10 via a wireless/cellular network 22 and/or wide area network (WAN) 24, including the Internet. The wide area network 24 may include additional networks, including an Internet of Things (IoT) network, among others. Connected to the wide area network 24 is a computing system comprising one or more servers 26 (e.g., 26A, . . . 26N).

The devices 20 may be embodied as a smartphone, mobile phone, cellular phone, pager, stand-alone image capture device (e.g., camera), laptop, tablet, personal computer, workstation, among other handheld, portable, or other computing/communication devices, including communication devices having wireless communication capability, including telephony functionality. In the depicted embodiment of FIG. 1, the device 20A is illustrated as a smartphone and the device 20B is illustrated as a laptop for convenience in illustration and description, though it should be appreciated that the devices 20 may take the form of other types of devices as explained above.

The devices 20 provide (e.g., relay) the (uncalibrated, raw) data sent by the antenna acquisition system 16 to one or more servers 26 via one or more networks. The wireless/cellular network 22 may include the necessary infrastructure to enable wireless and/or cellular communications between the device 20 and the one or more servers 26. There are a number of different digital cellular technologies suitable for use in the wireless/cellular network 22, including: 3G, 4G, 5G, GSM, GPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others, as well as Wireless-Fidelity (Wi-Fi), 802.11, streaming, etc., for some example wireless technologies.

The wide area network 24 may comprise one or a plurality of networks that in whole or in part comprise the Internet. The devices 20 may access the one or more server 26 via the wireless/cellular network 22, as explained above, and/or the Internet 24, which may be further enabled through access to one or more networks including PSTN (Public Switched Telephone Networks), POTS, Integrated Services Digital Network (ISDN), Ethernet, Fiber, DSL/ADSL, Wi-Fi, among others. For wireless implementations, the wireless/cellular network 22 may use wireless fidelity (Wi-Fi) to receive data converted by the devices 20 to a radio format and process (e.g., format) for communication over the Internet 24. The wireless/cellular network 22 may comprise suitable equipment that includes a modem, router, switching, etc.

The servers 26 are coupled to the wide area network 24, and in one embodiment may comprise one or more computing devices networked together, including an application server(s) and data storage. In one embodiment, the servers 26 may serve as a cloud computing environment (or other server network) configured to perform processing required to implement an embodiment of a neural network-based parametric inversion method and pixel-based inversion. When embodied as a cloud service or services, the server 26 may comprise an internal cloud, an external cloud, a private cloud, a public cloud (e.g., commercial cloud), or a hybrid cloud, which includes both on-premises and public cloud resources. For instance, a private cloud may be implemented using a variety of cloud systems including, for example, Eucalyptus Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture of the servers 26 may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, the servers 26 may be configured into multiple, logically-grouped servers (run on server devices), referred to as a server farm. The servers 26 may be geographically dispersed, administered as a single entity, or distributed among a plurality of server farms. The servers 26 within each farm may be heterogeneous. One or more of the servers 26 may operate according to one type of operating system platform (e.g., WINDOWS-based O.S., manufactured by Microsoft Corp. of Redmond, Wash.), while one or more of the other servers 26 may operate according to another type of operating system platform (e.g., UNIX or Linux). The group of servers 26 may be logically grouped as a farm that may be interconnected using a wide-area network connection or medium-area network (MAN) connection. The servers 26 may each be referred to as, and operate according to, a file server device, application server device, web server device, proxy server device, or gateway server device.

In one embodiment, one or more of the servers 26 may comprise a web server that provides a web site that can be used by users interested in the contents of the container 18 via browser software residing on a device (e.g., device 20). For instance, the web site may provide visualizations that reveal permittivity of the contents and/or geometric and/or other information about the container and/or contents (e.g., the volume geometry, such as cone angle, height of the grain along the container wall, etc.).

The functions of the servers 26 described above are for illustrative purpose only. The present disclosure is not intended to be limiting. For instance, functionality for performing the neural network-based parametric inversion and/or pixel-based inversion may be implemented at a computing device that is local to the container 18 (e.g., edge computing), or in some embodiments, such functionality may be implemented at the devices 20. In some embodiments, functionality of the neural network-based parametric inversion and/or pixel-based inversion may be implemented in different devices of the environment 10 operating according to a master-slave configuration or peer-to-peer configuration. In some embodiments, the antenna acquisition system 16 may bypass the devices 20 and communicate with the servers 26 via the wireless/cellular network 22 and/or the wide area network 24 using suitable processing and software residing in the antenna acquisition system 16.

Note that cooperation between the devices 20 (or in some embodiments, the antenna acquisition system 16) and the one or more servers 26 may be facilitated (or enabled) through the use of one or more application programming interfaces (APIs) that may define one or more parameters that are passed between a calling application and other software code such as an operating system, a library routine, and/or a function that provides a service, that provides data, or that performs an operation or a computation. The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer employs to access functions supporting the API. In some implementations, an API call may report to an application the capabilities of a device running the application, including input capability, output capability, processing capability, power capability, and communications capability.

An embodiment of a neural network-based parametric inversion system may include any one or a combination of the components of the environment 10. For instance, in one embodiment, the neural network-based parametric inversion system may include a single computing device (e.g., one of the servers 26 or one of the devices 20), and in some embodiments, the neural network-based parametric inversion system may comprise the antenna array 12, the antenna acquisition system 16, and one or more of the server 26 and/or devices 20. For purposes of illustration and convenience, implementation of an embodiment of a neural network-based parametric inversion method is described in the following as being implemented in a computing device that may be one of the servers 26, with the understanding that functionality may be implemented in other and/or additional devices.

Figures 2, 3:
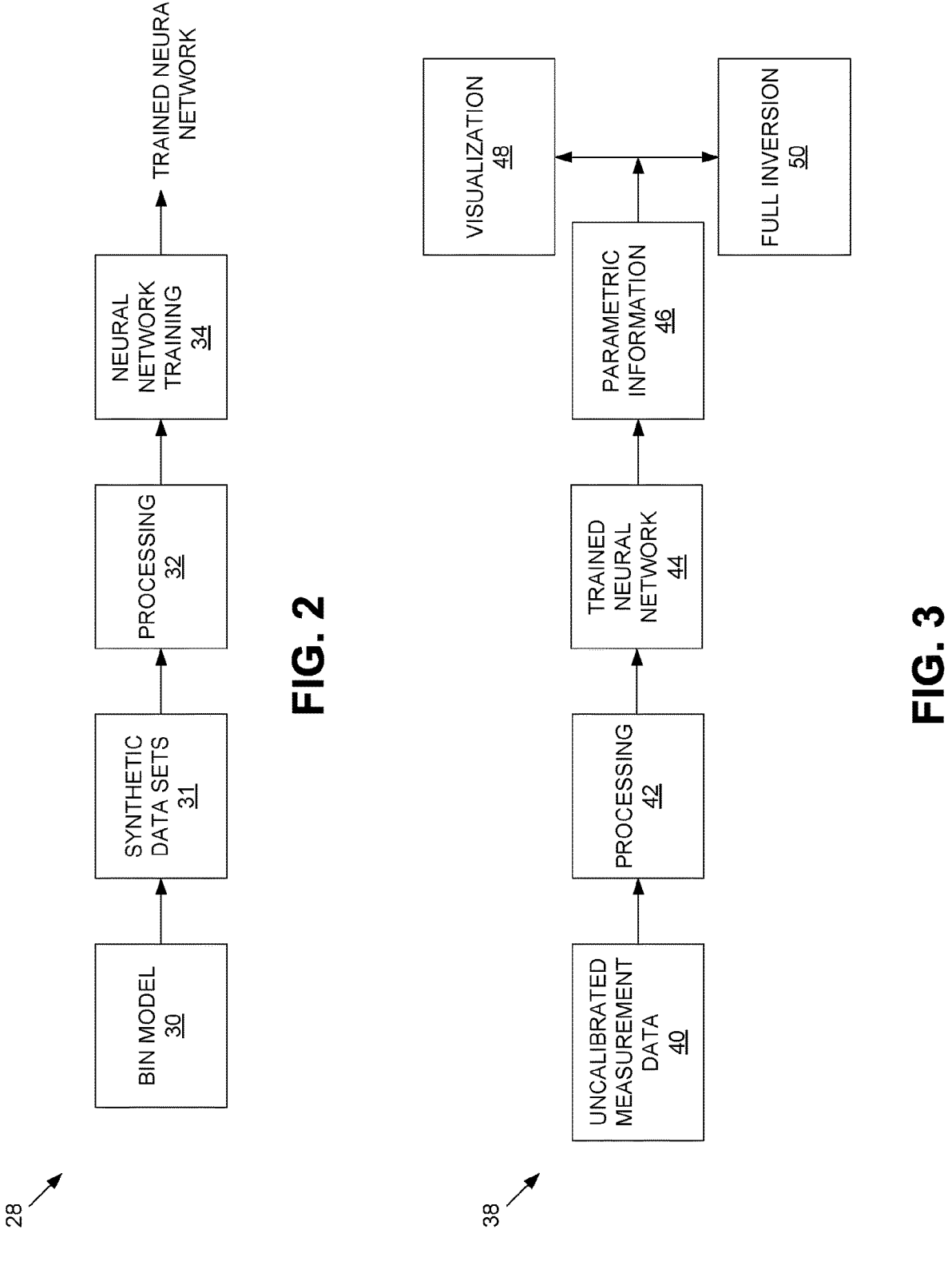
FIG. 2 is a logical flow diagram that illustrates synthetic data generation and neural network training for an embodiment of a neural network-based parametric inversion system.
FIG. 3 is a logical flow diagram that illustrates processing of uncalibrated measurement data via a neural network trained on synthetic data for an embodiment of a neural network-based parametric inversion system.

In one example operation (and assuming a neural network that has been trained using synthetic data, as described further in FIG. 2), a user (via the device 20) requests measurements of the contents of the container 18. This request is communicated to the antenna acquisition system 16. In some embodiments, the triggering of measurements may occur automatically based on a fixed time frame or based on certain conditions or based on detection of an authorized user device 20. In some embodiments, the request may trigger the communication of measurements that have already occurred. The antenna acquisition system 16 activates (e.g., excites) the antenna probes 14 of the antenna array 12, such that the acquisition system (via the transmission of signals and receipt of the scattered signals) collects a set of raw, uncalibrated electromagnetic data at a set of (a plurality of) discrete, sequential frequencies (e.g., 10-100 Mega-Hertz (MHz), though not limited to this range of frequencies nor limited to collecting the frequencies in sequence). In one embodiment, the uncalibrated data comprises total-field, S-parameter measurements (which are used to generate both a calibration model or information and a prior model or information as described below). As is known, S-parameters are ratios of voltage levels (e.g., due to the decay between the sending and receiving signal). Though S-parameter measurements are described, in some embodiments, other mechanisms for describing voltages on a line may be used. For instance, power may be measured directly (without the need for phase measurements), or various transforms may be used to convert S-parameter data into other parameters, including transmission parameters, impedance, admittance, etc. Since the uncalibrated S-parameter measurement is corrupted by the switching matrix and/or varying lengths and/or other differences (e.g., manufacturing differences) in the cables connecting the antenna probes 14 to the antenna acquisition system 16, it is important that embodiments of the neural network-based parametric inversion method use only magnitude (i.e., phaseless) data as input, which is relatively unperturbed by the measurement system. The antenna acquisition system 16 communicates (e.g., via a wired and/or wireless communications medium) the uncalibrated (S-parameter) data to the device 20, which in turn communicates the uncalibrated data to the server 26. At the server 26, data analytics are performed using a trained neural network as described in association with FIG. 3.

Referring now to FIG. 2, logical flow diagram 28 illustrates synthetic data generation and neural network training using the synthetic data for an embodiment of a neural network-based parametric inversion system. In some embodiments, the training is performed before the example sequence of operations described above in association with FIG. 1. For instance, once the container 18 (e.g., bin) and transceiver locations within that bin are specified, synthetic data generation may take place. Of course, if there is some standardization (e.g., industry standardization) of bins and antenna positions within the bin, then no additional data generation needs to take place for new bins with the same geometry as a previously trained network's bin. Further, as explained above, as experimental data becomes available, certain embodiments may use experimental data for training, alone or in combination with synthetic data. The blocks of the logical flow diagram 28 of FIG. 2, like the blocks of other logical flow diagrams described herein and depicted in the figures of the present application, are intended to represent modules of code (e.g., opcode, machine language code, higher level code), fixed or programmable hardware, or a combination of both that implement the functionality or method step of each block, where all blocks may be implemented in a single component or device or implemented using a distributed network of devices. Continuing, the logical flow diagram 28 comprises a bin model 30 (also, computer model, that comprises a forward model or forward solver), synthetic data sets 31, processing 32, and neural network training 34 that produces a trained neural network. In general, the logical flow diagram 28 illustrates the use of the bin model 30 that uses a forward solver to generate the synthetic data sets 31. The synthetic data sets 31 are processed 32 before passing to the neural network for training 34 resulting in a neural network that is trained on synthetic data. Once the neural network is trained on the synthetic data, the neural network may receive uncalibrated measurement data multiple times for the given container 18 (FIG. 1) to generate information in rapid fashion.

Figure 7:
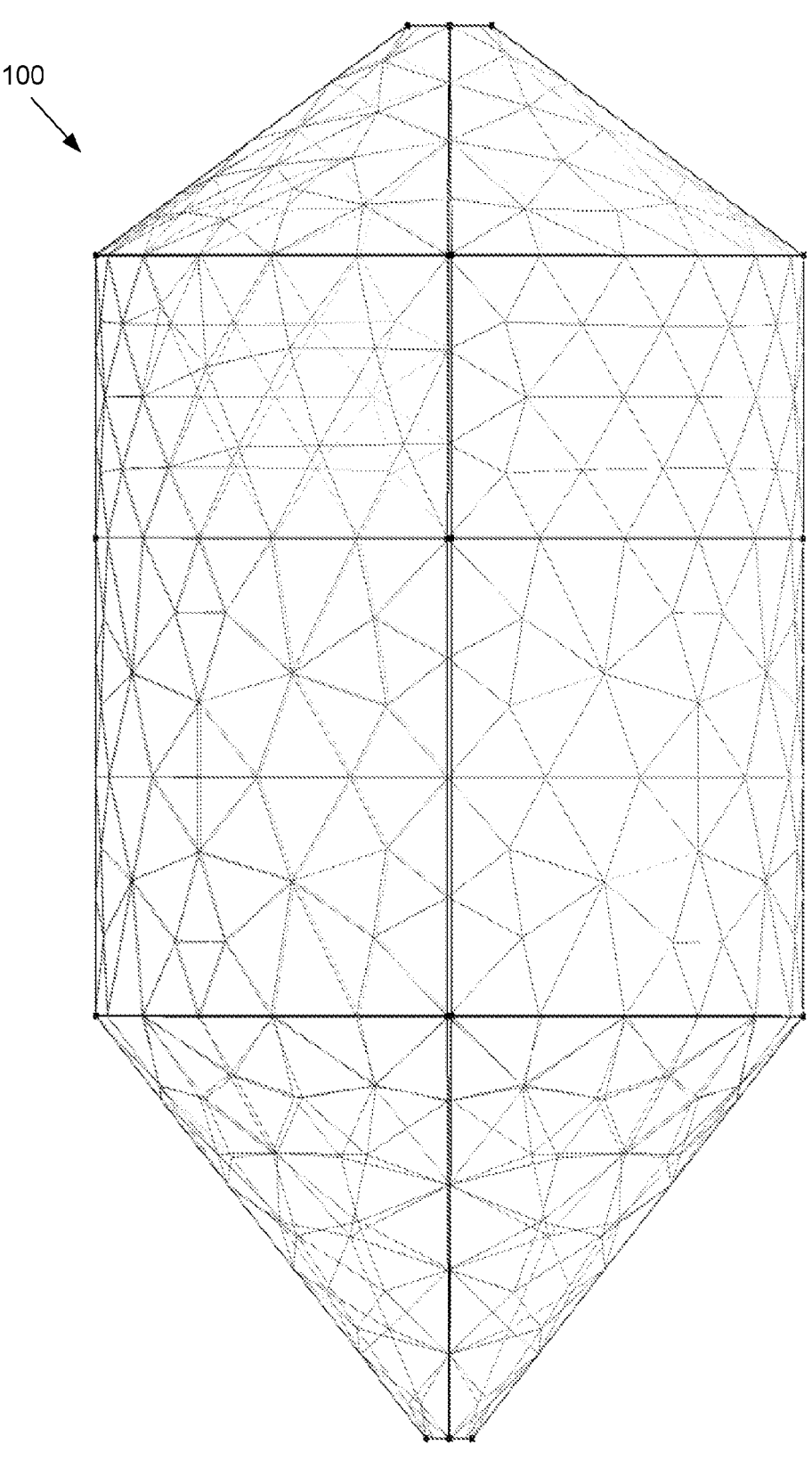
FIG. 7 is a schematic diagram that illustrates example results of a finite element model based on discretizing space inside a container using an embodiment of a neural network-based parametric inversion system.

The bin model 30 comprises a computer model of the container 18 (grain bin or the like and container 18 used interchangeably herein) using a known method (e.g., a discrete mesh). For instance, any one of several types of commercial, proprietary, free or open-source meshing software (e.g., GMSH) may be used to generate a 3D model of the container 18. Information about the container structure (e.g., diameter, height, etc.) may be input to the mesh software via a user interface or loaded from a file. The computer model 30 comprises a forward solver that simulates the electric and magnetic fields within the bin volume. The forward solver discretizes the bin geometry (surface and volume) into elements and computes the fields within each element. In one embodiment, the air/grain interface may, though not necessarily, be included in the geometry and a distinct mesh is produced for each unique geometry in the dataset. An example visualization of the computer model is shown in FIG. 7. For instance, the forward solver provides an initial estimate of the grain bin contents. In one embodiment, and referring also to FIG. 1, the forward solver is used to simulate the electromagnetic signals being received by the antenna array 12 (FIG. 1), at a set (or plurality) of selected frequencies. For instance, in one embodiment, the frequencies selected comprise a sub-set of the frequencies at which the electromagnetic signals were transmitted and collected by the acquisition system (e.g., approximately 1-10 of the frequencies collected by the transceiver system). In general, the electromagnetic solver estimates the electromagnetic fields for each simulated activation of a probe 14 of the antenna array 12 based on the 3D model of the container 18. In one embodiment, the electromagnetic solver comprises any one of a 3D finite-element method forward direct solver, a finite difference method, a method of moments, a discontinuous Galerkin method, or any other computational electromagnetic forward solver.

Explaining the forward solver further, in a "forward" solve, the contents of the bin are known and fields from those contents are simulated. The dataset comprises pairs of data: (e.g., bin contents, electromagnetic fields at the transceivers). The dataset is generated by sampling the space of all possible bin contents of interest and running a simulation to obtain the fields related to those bin-content-configurations. For instance, grain height (from a predetermined minimum to maximum in a defined step-size), angle (from a predetermined minimum to maximum using a defined step size), and real and imaginary permittivity (two values, each from a predetermined minimum to maximum with a defined, fixed step size) is sampled, and the bin model 30 considers all possible combinations of height, angle and permittivity values and runs the forward solver to generate the synthetic data 31 associated with each configuration, using a plurality of frequencies that are also used to train the neural network. In some embodiments, angle may be replaced with volume (e.g., from volume and height, the angle may be obtained, and from angle and height, the volume may be obtained). In some embodiments, permittivity may be replaced with moisture information via mapping of discrete values of moisture to permittivities through modelling.

Note that the estimated parameters listed above are illustrative of a particular container geometry as indicated in FIG. 1, and that in some applications, the container may be of a different geometry or different inlet/outlet ports and/or port quantities that may engender different parameter estimates. Also, though an air/grain interface is described here for illustrative purposes, it should be appreciated by one having ordinary skill in the art that other types of interfaces (e.g., water/fuel) or different quantities of interfaces (e.g., water/fuel/air) may need to be modeled, and as such, in some embodiments, the modeled parameters may comprise geometric parameters that describe one or more interfaces between various contents of the container.

In the generation of the synthetic data 31, the forward solver of the bin model 30 may be called multiple times for each of a plurality of meshes to generate combinations of real and imaginary permittivities for each height and angle combination. Accordingly, the synthetic data may comprise one or any combination of grain height and/or grain volume, cone angle, bulk real permittivity, and bulk imaginary permittivity.

Figures 5A, 5B:
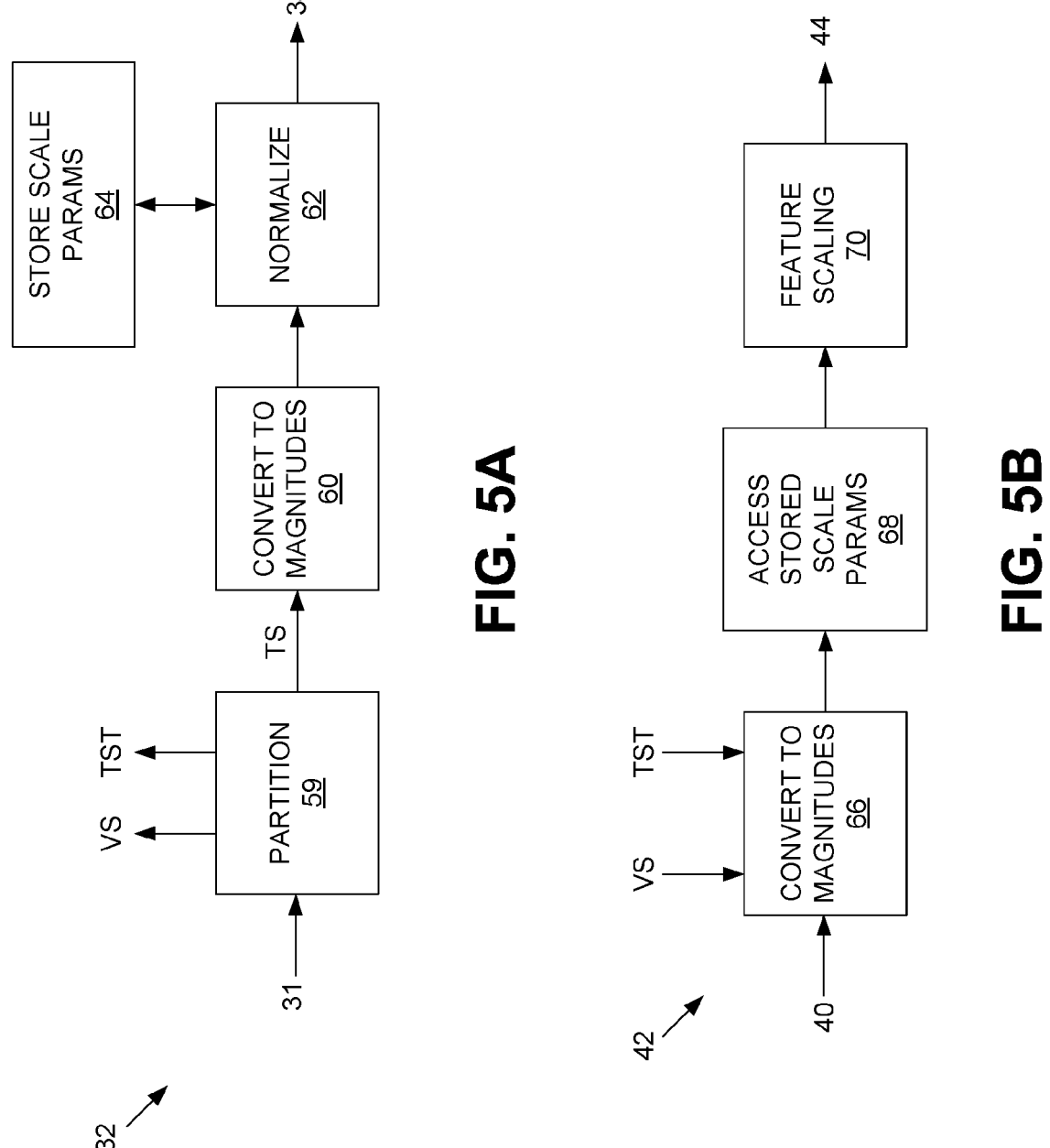
FIG. 5A is a logical flow diagram that illustrates example normalization of a training set for an embodiment of a neural network-based parametric inversion system.
FIG. 5B is a logical flow diagram that illustrates example scaling of validation and test data in a manner that experimental data is to be scaled for an embodiment of a neural network-based parametric inversion system.

The synthetic data 31 undergoes processing 32. FIG. 5A shows an embodiment of the processing 32 that is performed on the synthetic data 31. The synthetic data undergoes partitioning 59 to derive a training set (TS), a validation set (VS), and a test set (TST) (referred to herein also as a synthetic test set to distinguish it from the experimental data to which the neural network is ultimately applied). Digressing briefly, partitioning is used in machine learning, where a neural network is trained with a part of the dataset (e.g., the training set) and the training process performs validation throughout training (e.g., a validation set) and the resulting machine learning model is applied to a test set to gauge performance. The validation and test data undergo processing 42 (see FIG. 5B) whereby the validation and test sets are scaled in a manner that the experimental data is scaled. Generally speaking, all three datasets (training, validation, and test) are passed from processing 32 to neural network training 34 to produce the trained neural network. The validation and test sets are simply used during this training procedure to validate accurate performance of the neural network.

The training set undergoes conversion to magnitude 60 (e.g., magnitude of voltage, and not the phase). The training set comprises magnitude and phase information, though the phase information from the physical domain (experimental, S-parameter data) is corrupted from various features of the physical domain (e.g., cable losses/phase shifts, switch path losses, corrupted signals due to the presence of plural antennas, receiver thermal noise, etc.). Accordingly, the phase information is removed in the conversion 60, the phaseless or magnitude only conversion performed to enable a valid later-implemented comparison between synthetic and experimental data.

The magnitude-only training set is normalized 62. That is, the use of neural networks does not circumvent scaling issues between the raw S-parameters and the simulated fields. The data normalizations described herein enables the neural network training on synthetic data while enabling successful operations on experimental data without calibration. In one embodiment, the magnitude-only training set comprises a plurality of samples of projected field measurements at the field probes 14 (FIG. 1), referred to herein as $|H_\phi|$ (magnetic fields in amperes/meter) at a plurality of different frequencies $n_f$. Using an illustrative, non-limiting example, assume 24 transmitters and 23 receivers per transmitter (e.g., 552 data samples). To combine the data from multiple frequencies, the 552 samples of $|H_\phi|$ are first flattened for each of the $n_f$ frequencies, and are vertically concatenated to create an input column vector that is $552 \times n_f$ elements long. Equivalently, this vector is a flattened version of $|H_\phi|$. Each feature ($|H_\phi|_{i,j}$ for a given frequency) is normalized across all samples in the training set using, in one embodiment, z-scores, and the normalized features are provided to the neural network for training 34. Note that scale parameters are stored 64 for use in the processing 42 of FIG. 5B. For instance, the mean and standard deviation ($\mu_{train}$, $\sigma_{train}$) are stored 64. Based on the processing 32, the synthetically trained neural network may be applied to uncalibrated experimental data. The processed data is provided to the neural network for training 34, the neural network described below in association with FIG. 4.

Referring to FIG. 3, shown is a logical flow diagram 38 that illustrates processing of uncalibrated measurement data via a neural network trained on synthetic data for an embodiment of a neural network-based parametric inversion system. The logical flow diagram 38 comprises uncalibrated measurement data 40, processing 42, a trained neural network 44, parametric information 46, visualization 48 and full inversion 50. In general, the process shown in FIG. 3 receives uncalibrated measurement data 40 from the antenna acquisition system 16 (FIG. 1) directly or via the devices 20, performs processing 42, and applies the trained neural network 44 to the processed data to derive parametric information (e.g., prediction parameters including height, angle, volume, complex permittivity, moisture, etc.) 46, which may be rendered on a display 48 or used for full inversion 50.

Referring to the receipt of uncalibrated measurement data 40, a set of electromagnetic data are collected by the transmitter/receiver system depicted in FIG. 1 at a set of discrete sequential (and/or non-sequential) frequencies. As explained above, the uncalibrated measurement data 40 comprises total-field, S-parameter measurements extracted from the experimental data. These complex measurements undergo processing 42, as shown in FIG. 5B. Referring now to FIG. 5B, the processing 42 comprises conversion of the S-parameter measurements to magnitudes 66, accessing stored scale parameters 68 (e.g., from the storage of those parameters in 64, FIG. 5A), and the implementation of feature scaling 70. For the processing 42 in general, the data from the set of frequencies (the same frequencies used to train the neural network) are combined (vertically concatenated) and passed to the trained neural network 44. More specifically, the complex S-parameters from the experimental data are converted to magnitude only data 66 (e.g., removal of phase information). In one embodiment, reciprocity is enforced by combining the transmitter/receiver pair (m, n) and (n, m) values as an average. In an attempt to mitigate the unknown cable and switch losses associated with each sample, the S-matrix magnitude data is normalized independently along each row (i.e., corresponding to each transmitter and thus associated with different loss in the transmitting cable) to zero mean and unit variance. Thus, the magnitude only S parameter data is processed in the same or similar way as the synthetic data (e.g., transmitter-wise normalization as explained above) followed in one embodiment by scaling 70 to the mean and standard deviation of the training data (i.e., so that the normalized and scaled S-parameter data can be appropriately compared to synthetic neural network training data). Similarly, the (magnitude-only) validation and testing sets (both synthetic and experimental) are feature scaled 70 using $\mu_{train}$, $\sigma_{train}$ to scale their values to match the distribution of the training set.

Figure 8:
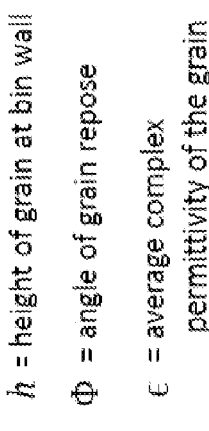
FIG. 8 is a schematic diagram that illustrates an example visualization of contents of a grain bin based on implementation of an embodiment of a neural network-based parametric inversion system.
Figure 8:
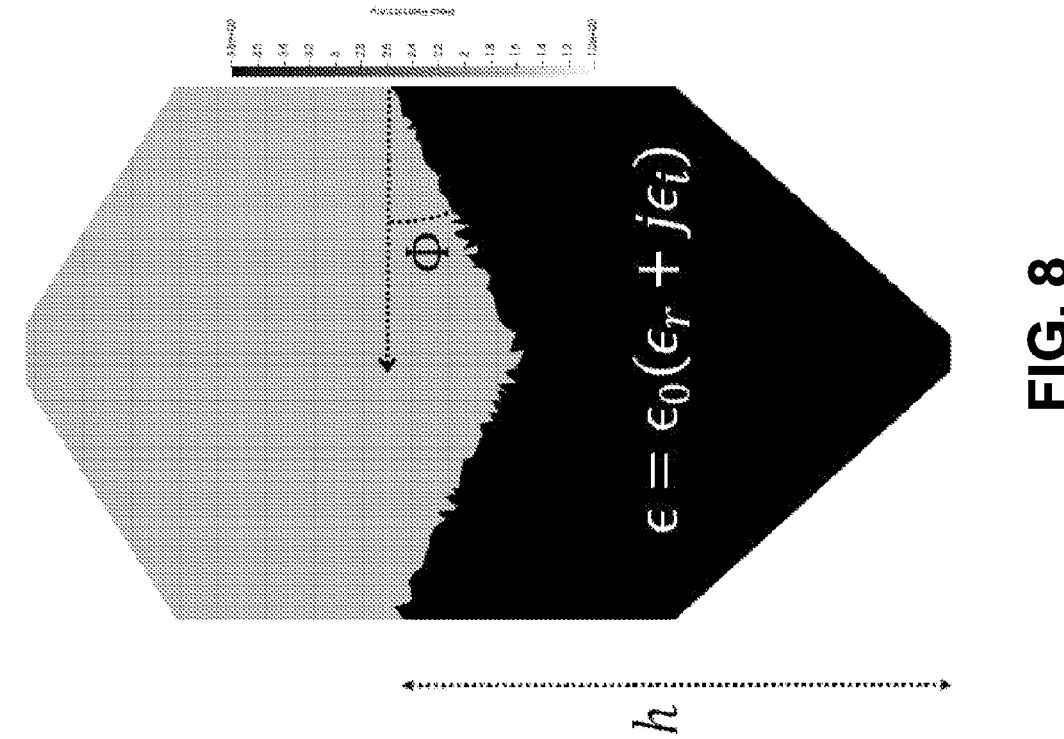
Figure 8:
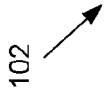

Referring back to FIG. 3, the processed data 42 is provided to the trained neural network 44, which in turn computes parametric information 46 (e.g., prediction parameters) that may be used for visualization 48 and/or full inversion 50. For instance, the parametric information 46 may comprise the grain permittivity (e.g., imaginary and real values) and geometric information about the grain or grain volume (e.g., grain height and cone angle or volume). In some embodiments, the parametric information 46 may be used as feedback in a visualization 48 (e.g., data presented on a screen). In some embodiments, the output comprises a more fully developed visualization of these parameters based on applying these parameters to a known, finite element mesh or other known visualization algorithm (e.g., contrast source inversion). That is, the parametric information 46 may be used in a pixel-based inversion algorithm (e.g., instead of four values in this example, there may be thousands or more, as shown in FIG. 8). In FIG. 8, every pixel or voxel element is ascribed a complex permittivity (real and imaginary). In other words, the neural network-based parametric inversion method comprises a pre-processing step or steps (e.g., of obtaining the prior information and calibration data) to the pixel-based inversion to derive the visualization of, for instance, the visualization shown in FIG. 8. The use of the parametric information 46 in a subsequent pixel based inversion is within the abilities of one having ordinary skill in the art, and hence further discussion herein is omitted.

Note that the description above refers to model parameters that include volume and angle, though in some embodiments, other model parameters may be used, including surface models.

Figure 4:
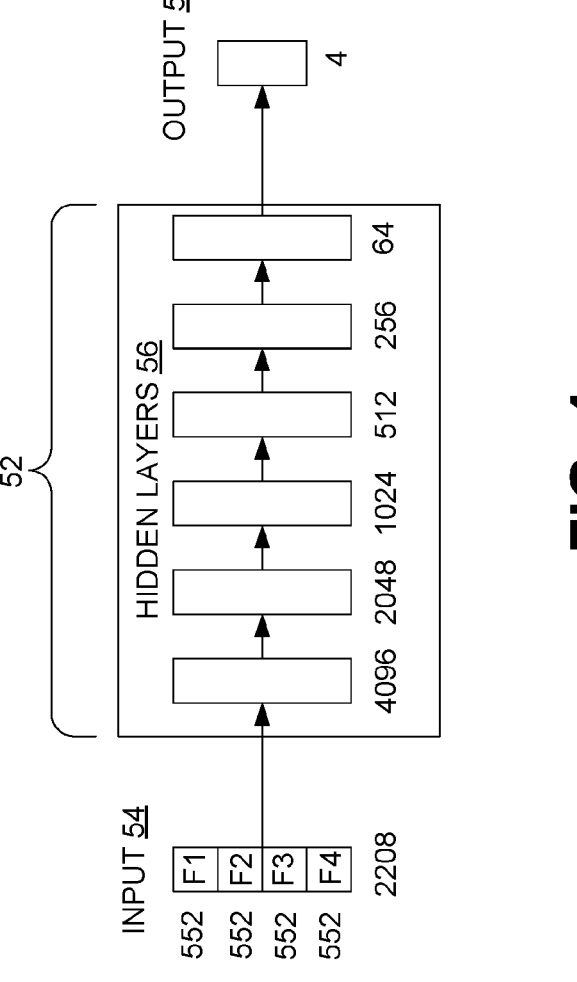
FIG. 4 is a schematic diagram that illustrates an embodiment of an example neural network used in an embodiment of a neural network-based parametric inversion system.

Referring now to FIG. 4, shown is a neural network 52 that is trained in one embodiment by the synthetic data and then used on experimental S-parameter (e.g., ratios of voltages) data to derive prediction parameters. In one embodiment, the neural network 52 receives the training data (training set) or experimental S-parameter data, processes the data via one or more hidden layers 56 (six shown for an example illustration), and provides an output 58 of the prediction parameters. Using an illustrative example of data sets for four (4) different frequencies using a 24×23 transmitter/receiver system, as indicated above for illustration, results in 552 samples for each frequency (F1-F4) representing a total of 2208 (552×4) data samples input to the neural network 52. Each layer of the hidden layers 56 is shown illustratively with the quantity of neurons per layer (e.g., 4096 under the first layer, 2048 under the second layer, etc.), with the output 58 comprising four output values pertaining to the trained or experimental predictive parameters (e.g., angle or volume, real permittivity, imaginary permittivity) based on the last layer of 64 neurons. These four parameters may characterize the grain/air interface and provide average permittivity of the grain in the bin to provide information for inventory management, including grain volume and an estimate of moisture content in the bin. These parameters can further be used to calibrate the raw data for full inversions.

In one embodiment, the neural network 52 uses a supervised learning method (e.g., relying on a dataset of fields and parameters). More importantly, the neural network is trained on synthetic data. As the training and use of neural networks are known to those having ordinary skill in the art, further discussion of the same is omitted here for brevity. With regard to the experimental data, the output 58 may be used to generate the volume of the grain in the bin and the average moisture content of the grain in the bin (e.g., information about the grain), which is useful information that may be provided via a user interface to render feedback and/or transmitted and/or stored for later processing or review (e.g., in the way of reports).

Figure 6:
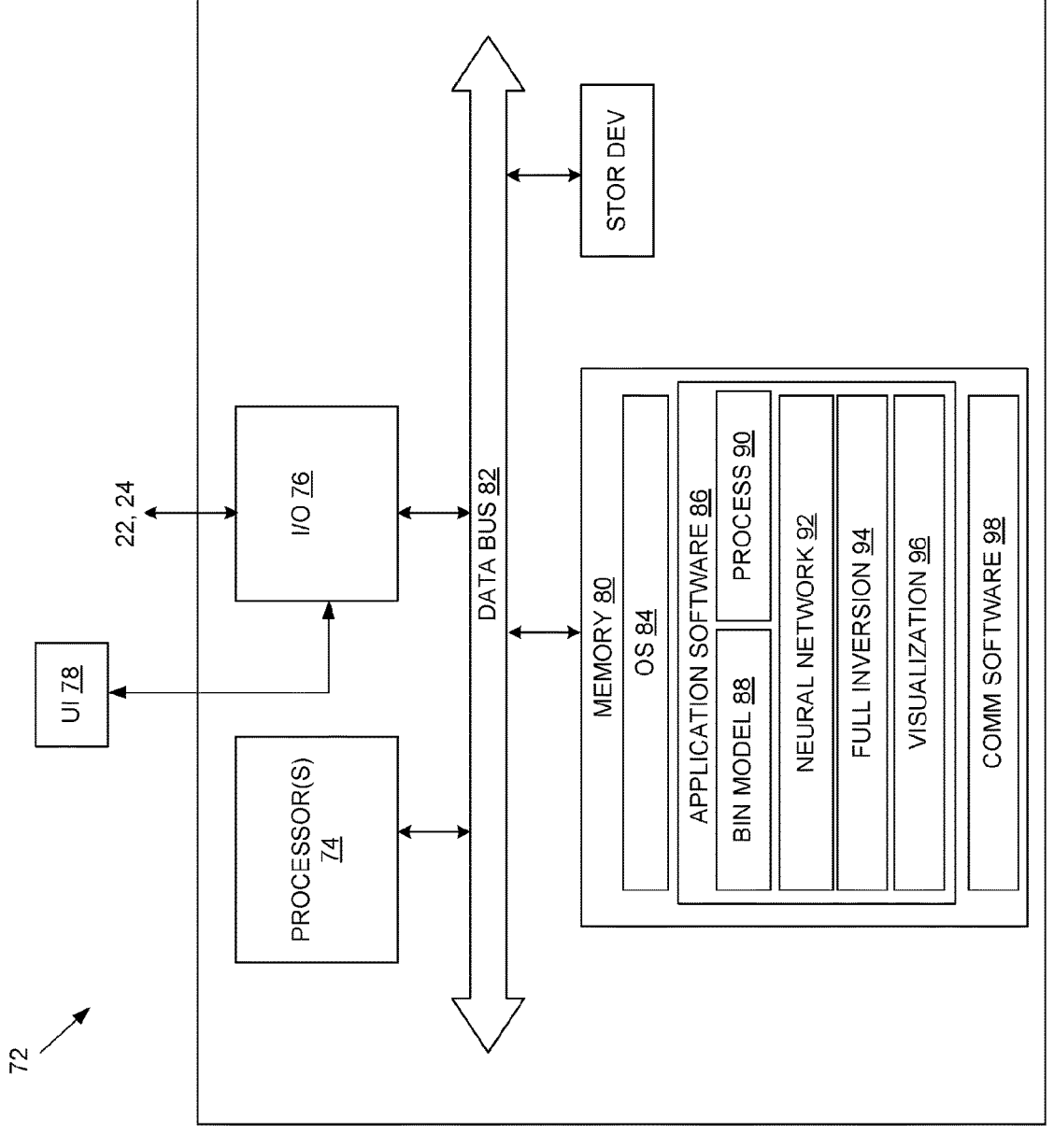
FIG. 6 is a block diagram that illustrates an embodiment of an example computing device of an embodiment of a neural network-based parametric inversion system.

Having described an embodiment of a neural network-based parametric inversion system, attention is directed to FIG. 6, which illustrates an example computing device 72 used in one embodiment of the neural network-based parametric inversion system depicted in FIG. 1. In one embodiment, the computing device 72 may be one of the servers 26 or one of the devices 20. Though described as implementing certain functionality of a neural network-based parametric inversion method, in some embodiments, such functionality may be distributed among plural devices (e.g., using plural, distributed processors) that are co-located or geographically dispersed. In some embodiments, functionality of the computing device 72 may be implemented in another device, including a programmable logic controller, ASIC, FPGA, among other processing devices. It should be appreciated that certain well-known components of computers are omitted here to avoid obfuscating relevant features of computing device 72. In one embodiment, the computing device 72 comprises one or more processors, such as processor 74, input/output (I/O) interface(s) 76, a user interface 78, and memory 80, all coupled to one or more data busses, such as data bus 82. The memory 80 may include any one or a combination of volatile memory elements (e.g., random-access memory RAM, such as DRAM, and SRAM, etc.) and nonvolatile memory elements (e.g., ROM, hard drive, tape, CDROM, etc.). The memory 80 may store a native operating system, one or more native applications, emulation systems, or emulated applications for any of a variety of operating systems and/or emulated hardware platforms, emulated operating systems, etc. In the embodiment depicted in FIG. 6, the memory 80 comprises an operating system 84 and application software 86.

In one embodiment, the application software 86 comprises a bin model 88 having one or more forward solvers as explained above, a process module 90 (e.g., for implementing the process 32 and 42), a neural network 92 (as described in association with FIG. 4), full inversion software 94, visualization software 96, and communication software 98 that formats data according to the appropriate format to enable transmission or receipt of communications over the networks and/or wireless or wired transmission hardware (e.g., radio hardware). In general, the application software 86 performs the functionality described in association with the logical flow diagrams 28 and 38, as well as the neural network 52 and processing 32 and 42, in FIGS. 2-5B. The full inversion software 94 may comprise known pixel-based inversion (PBI) software. For instance, the full inversion software 94 comprises known algorithms for performing pixel-based inversion based on the outputs provided by the neural network 92, and includes contrast source inversion or other known visualization software. In some embodiments, one or more functionality of the application software 86 may be implemented in hardware. In some embodiments, one or more of the functionality of the application software 86 may be performed in more than one device. It should be appreciated by one having ordinary skill in the art that in some embodiments, additional or fewer software modules (e.g., combined functionality) may be employed in the memory 80 or additional memory. In some embodiments, a separate storage device may be coupled to the data bus 82, such as a persistent memory (e.g., optical, magnetic, and/or semiconductor memory and associated drives).

The processor 74 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the computing device 72.

The I/O interfaces 76 provide one or more interfaces to the networks 22 and/or 24. In other words, the I/O interfaces 76 may comprise any number of interfaces for the input and output of signals (e.g., analog or digital data) for conveyance over one or more communication mediums.

The user interface (UI) 78 may be a keyboard, mouse, microphone, touch-type display device, head-set, and/or other devices that enable visualization of the contents and/or container as described above. In some embodiments, the output may include other or additional forms, including audible or on the visual side, rendering via virtual reality or augmented reality based techniques.

Note that in some embodiments, the manner of connections among two or more components may be varied. Further, the computing device 72 may have additional software and/or hardware, or fewer software.

The application software 86 comprises executable code/instructions that, when executed by the processor 74, causes the processor 74 to implement the functionality shown and described in association with the neural network-based parametric inversion method, including functionality described in association with FIGS. 1-5B (and FIG. 9 below). As the functionality of the application software 86 has been described in the description corresponding to the aforementioned figures, further description here is omitted to avoid redundancy.

Execution of the application software 86 is implemented by the processor 74 under the management and/or control of the operating system 84. In some embodiments, the operating system 84 may be omitted. In some embodiments, functionality of application software 86 may be distributed among plural computing devices (and hence, plural processors).

When certain embodiments of the computing device 72 are implemented at least in part with software (including firmware), as depicted in FIG. 6, it should be noted that the software can be stored on a variety of non-transitory computer-readable medium (including memory 80) for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 72 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

FIG. 7 is a schematic diagram 100 that illustrates example results of a finite element model, described above, based on discretizing space inside a container using an embodiment of a neural network-based parametric inversion method.

FIG. 8 is a schematic diagram 102 that illustrates an example visualization of contents of a grain bin based on implementation of an embodiment of a neural network-based parametric inversion method. As shown, the visualization may include parameter values describing permittivity and geometric information about the contents, including the height of the grain along the container wall, the angle of grain repose, and the average complex permittivity of the grain. In some embodiments, the rendering of the color of the grain may be indicative of average grain moisture content, among other parameters.

Figure 9:
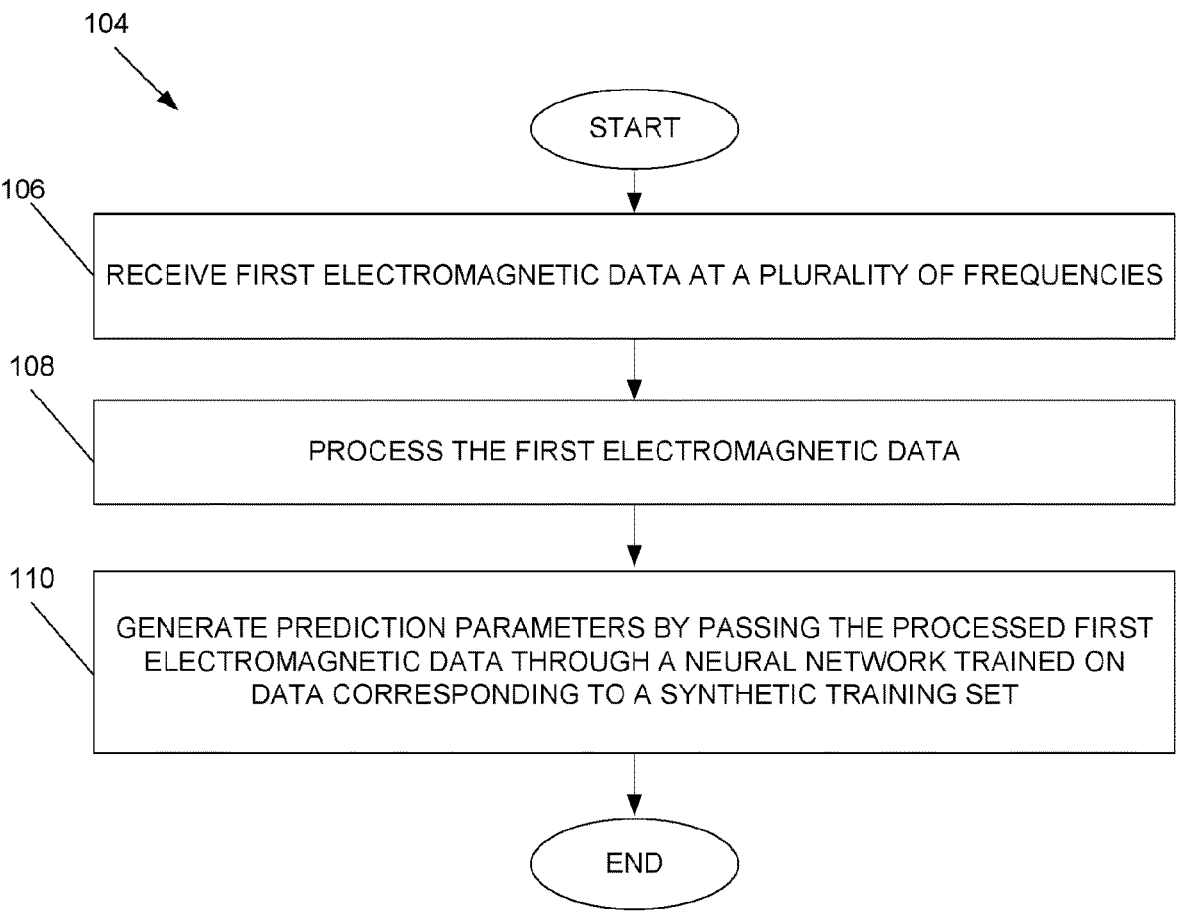
FIG. 9 is a flow diagram that illustrates an embodiment of an example neural network-based parametric inversion method.

Having described certain embodiments of a neural network-based parametric inversion system, it should be appreciated within the context of the present disclosure that one embodiment of a neural network-based parametric inversion method, denoted as method 104 and illustrated in FIG. 9, and implemented using one or more processors (e.g., of a computing device or plural computing devices), comprises receiving first electromagnetic data at a plurality of frequencies (106); processing the first electromagnetic data (108); and generating prediction parameters by passing the processed first electromagnetic data through a neural network trained on data corresponding to a synthetic training set, the prediction parameters corresponding to a container and contents located within the container (110).

Figure 10:
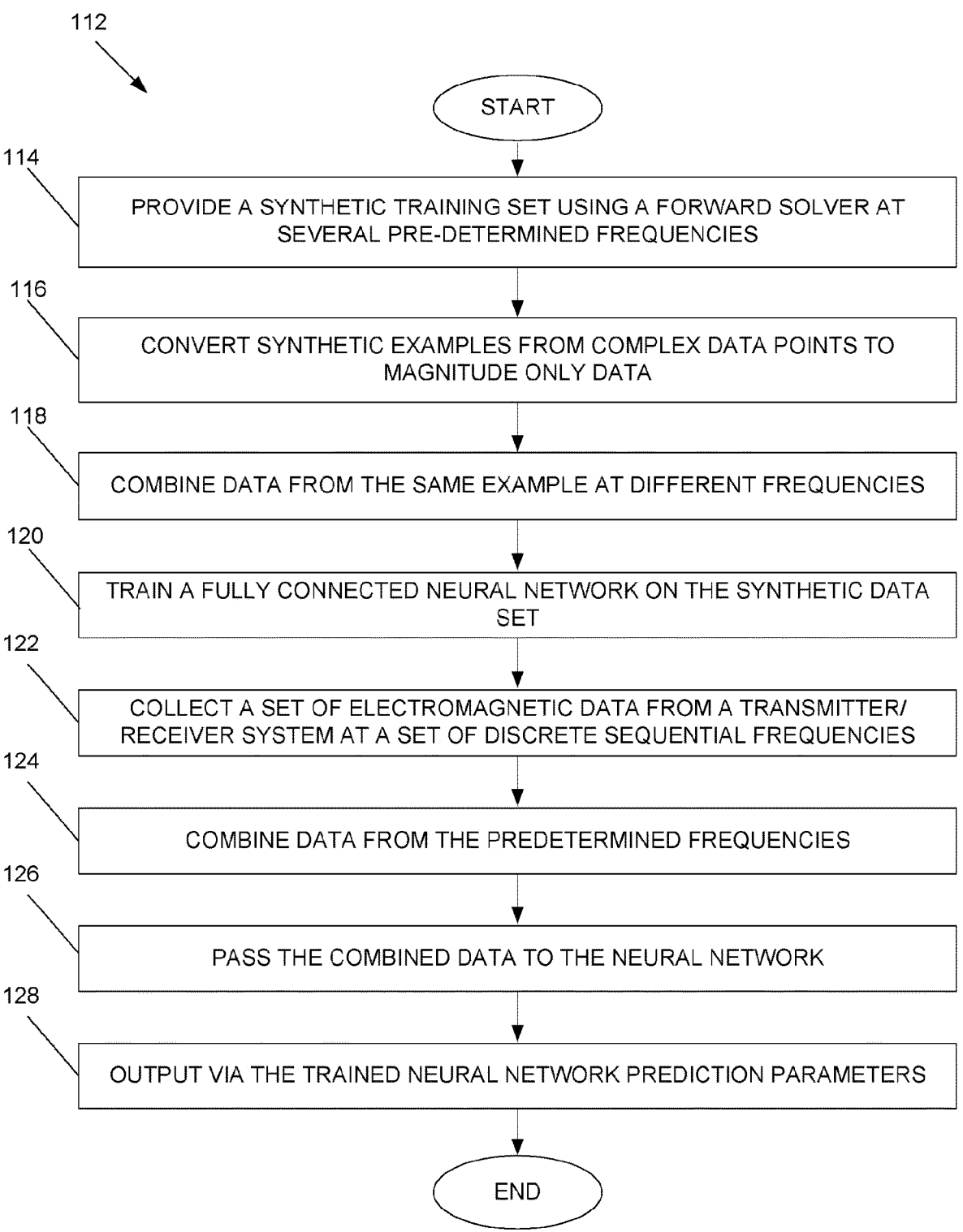
FIG. 10 is a flow diagram that illustrates another embodiment of an example neural network-based parametric inversion method.

FIG. 10 provides yet another embodiment of a neural network-based parametric inversion method, denoted as method 112, and comprises (with example, non-limiting illustrations indicated in parenthesis) providing (e.g., producing) a synthetic training set (e.g., tens of thousands of examples) using a forward solver at several (e.g., 4-8) pre-determined frequencies (114); converting synthetic examples from complex data points to magnitude only data (116); combining data from the same example at different frequencies (e.g., vertically concatenated) (118); training a fully connected neural network (e.g., with six (6) hidden layers and four (4) outputs as shown in FIG. 4) on the synthetic data set (120); collecting a set of electromagnetic data from a transmitter/receiver system (e.g., FIG. 1) at a set of discrete sequential frequencies (122); combining (e.g., vertically concatenating) data from the predetermined frequencies (the same frequencies used to train the neural network) (124); passing the combined data to the neural network (126); and outputting via the trained neural network prediction parameters (e.g., four prediction parameters) (128).

Any process descriptions or blocks in flow diagrams should be understood as representing logic (software and/or hardware) and/or steps in a process, and alternate implementations are included within the scope of the embodiments in which functions may be executed out of order from that shown or discussed, including substantially concurrently, or with additional steps (or fewer steps), depending on the functionality involved, as would be understood by those reasonably skilled in the art of the present disclosure.

Certain embodiments of a neural network-based parametric system and method provide for training of the neural network using synthetic data, thus not requiring experimental measurements to be trained. That is, the neural network is capable of being trained solely on synthetic examples, and can be used to analyze experimental data without modification to the network, thus enabling ready field use shortly after the installation location of antennas in the bin is known.

It should be emphasized that the above-described embodiments of the present disclosure are merely possible examples of implementations, merely set forth for a clear understanding of the principles of the disclosure. Many variations and modifications may be made to the above-described embodiment(s) of the disclosure without departing substantially from the scope of the disclosure. All such modifications and variations are intended to be included herein within the scope of this disclosure and protected by the following claims.

The invention claimed is:

1. A system, comprising: one or more processors; and a memory comprising instructions, wherein the one or more processors are configured by the instructions to:

(a) from an acquisition system comprising an electromagnetic transceiver and a radio frequency (RF) antenna array coupled thereto that comprises a plurality of antenna probes that are distributed around an interior holding space of a container and are operable by said electromagnetic transceiver in transmitter/receiver pairs to impart RF energy to held contents of the container from transmitting antennae of said transmitter/receiver pairs and collect resulting scattered RF signals from receiving antennae of said transmitter/receiver pairs, receive first uncalibrated electromagnetic data at a plurality of radio frequencies, which first uncalibrated electromagnetic data comprises S-parameter measurements composed of both magnitude and phase;

(b) process the first uncalibrated electromagnetic data to derive therefrom a phaseless and magnitudinally normalized electromagnetic dataset that preserves magnitudinal information from the S-parameter measurements, normalized transmitter-wise, and disregards phase; and (c) generate prediction parameters for said container and said contents thereof by passing the phaseless and magnitudinally normalized electromagnetic dataset through a neural network trained on likewise phaseless and magnitudinally normalized data corresponding to a synthetic training set previously derived using a computer model of the container and simulated antenna probes.

2. The system of claim 1, wherein prior to receiving the first electromagnetic data, the one or more processors are further configured by the instructions to generate the synthetic training set using a forward solver of said computer model at a plurality of predetermined frequencies, the synthetic training set corresponding to second electromagnetic data comprising synthetic prediction parameters of a same type as the prediction parameters.

3. The system of claim 2, wherein the forward solver comprises any one of a 3D finite-element method forward direct solver, a finite difference method, a method of moments, discontinuous Galerkin method, or computational electromagnetic forward solver.

4. The system of claim 2, wherein the one or more processors are further configured by the instructions to process the second electromagnetic data from an originally complex data format composed of both phase and magnitude to a phaseless dataset that preserves magnitudinal information from the second electromagnetic data, but disregards phase.

5. The system of claim 4, wherein the one or more processors are further configured by the instructions to combine magnitude values of said phaseless dataset at each of the plurality of frequencies.

6. The system of claim 5, wherein the one or more processors are further configured by the instructions to process phaseless dataset by normalizing the magnitude values, and to pass a result of the combining and normalization to the neural network, the neural network configured to train on the result.

7. The system of claim 1 wherein the processing of the first uncalibrated electromagnetic data comprises conversion thereof to a phaseless dataset void of phase information, and combining magnitude values of the phaseless dataset at each of the plurality of frequencies.

8. The system of claim 7, wherein the processing of the first uncalibrated electromagnetic data further comprises normalizing the magnitude values, and the one or more processors are further configured by the instructions to pass a result of the combination and normalization to the neural network, the neural network processing the result based on the data corresponding to the synthetic training set.

9. The system of claim 8, wherein the result corresponds to electromagnetic field estimates for different values for each of plural synthetic prediction parameters of the container and the contents held within the container.

10. The system of claim 9, wherein the plural synthetic prediction parameters comprise a height of the contents along a side wall of the container, a cone angle of the contents extending from the side wall to approximately a peak location of the contents, and a complex permittivity of the contents.

11. The system of claim 10, wherein the contents comprises a raw vegetable product and the container comprises a storage bin for the raw vegetable product.

12. The system of claim 1, wherein the neural network comprises plural hidden layers.

13. The system of claim 1, wherein the neural network is trained on the data corresponding to the synthetic training set only once for the container and the trained neural network generates prediction parameters at a plurality of different times based on the receipt of updated electromagnetic data.

14. The system of claim 1, wherein the plurality of frequencies are predetermined.

15. The system of claim 1, wherein the system comprises said acquisition system, from which the first uncalibrated electromagnetic data is received directly or via one or more intervening devices.

16. The system of claim 1, wherein the one or more processors are further configured by the instructions to provide a visualization of the container and geometries of the contents within the container.

17. The system of claim 1, wherein the one or more processors are further configured by the instructions to provide moisture content values of the contents within the container based on the prediction parameters.

18. A non-transitory, computer readable medium comprising instructions, that when executed by one or more processors, causes the one or more processors to perform steps (a) through (c) of claim 1.

* * * * *